United States Patent [19]

Lesher et al.

[11] 4,309,537

[45] Jan. 5, 1982

[54] PRODUCTION OF IMIDAZO[4,5-b]PYRIDIN-2-ONES OR THIONES

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 236,147

[22] Filed: Feb. 20, 1981

Related U.S. Application Data

[62] Division of Ser. No. 135,105, Mar. 28, 1980.

[51] Int. Cl.³ .................. C07D 471/04; C07D 413/14; C07D 401/14
[52] U.S. Cl. .................................... 544/127; 546/256; 546/257
[58] Field of Search ................. 546/256, 257; 544/127

[56] References Cited

PUBLICATIONS

Baldwin et al., *Jour. of Medicinal Chemistry*, vol. 20, pp. 1189–1193 (1977).

*Primary Examiner*—John M. Ford
*Attorney, Agent, or Firm*—Robert K. Bair; B. Woodrow Wyatt

[57] ABSTRACT

1,3-Dihydro-1-$R_1$-3-$R_3$-6-PY-5-Q-2H-imidazo[4,5-b]pyridin-2-ones or -2-thiones or pharmaceutically-acceptable acid-addition salts thereof, which are useful as cardiotonic agents, where Q is hydrogen or lower-alkyl, $R_1$ and $R_3$ are each hydrogen, lower-alkyl, lower-hydroxyalkyl, 2,3-dihydroxypropyl, lower-alkoxyalkyl or Y-NB where Y is lower-alkylene and NB is di-(lower-alkyl)amino or 4-morpholinyl, at least one of $R_1$ and $R_3$ being hydrogen, and PY is 4- or 3-pyridinyl or 4- or 3-pyridinyl having one or two substituents, are prepared by reacting a 2-$R_3$NH-3-$R_1$NH-5-PY-6-Q-pyridine with urea or carbonyldiimidazole to produce said -2-one or with an alkali metal xanthate, thiourea or thiocarbonyldiimidazole to produce said -2-thione. Also shown and claimed are cardiotonic compositions and a method for increasing cardiac contractility using said cardiotonic agents. Also shown are processes for preparing said intermediate 2-$R_3$NH-3-$R_1$NH-5-PY-6-Q-pyridines and other intermediates used in said processes.

1 Claim, No Drawings

PRODUCTION OF IMIDAZO[4,5-b]PYRIDIN-2-ONES OR THIONES

CROSS-REFERENCE TO RELATED APPLICATION

This is a division of application Ser. No. 135,105, filed Mar. 28, 1980.

The intermediate 2-$R_3$NH-3-$R_1$NH-5-PY-6-Q-pyridines and intermediates therefore and preparation thereof, which are shown herein, where $R_1$, $R_3$, PY and Q are defined hereinbelow, are disclosed claimed in copending patent application Ser. No. 135,100, filed Mar. 28, 1980.

BACKGROUND OF THE INVENTION (a) Field of the Invention

This invention relates to 2H-imidazo[4,5-b]pyridin-2-ones and -2-thiones, their preparation and their use as cardiotonics.

(b) Description of the Prior Art

Baldwin et al [J. Med. Chem. 20, 1189–1193 (1977)] prepared 2-(3-pyridinyl)-1H-imidazo[4,5-b]pyridine and 2-(4-pyridinyl)-1H-imidazo[4,5-b]pyridine by heating respectively, a mixture of 2,3-diaminopyridine and nicotinic acid or a mixture of 2,3-diaminopyridine and nicotinic acid or a mixture of 2,3-diaminopyridine and isonicotinic acid. Both of these compounds were found by Baldwin et al to be inactive when tested as inhibitors of xanthine oxidase.

SUMMARY OF THE INVENTION

In a composition of matter aspect, the invention relates to 1,3-dihydro-1-$R_1$-3-$R_3$-6-PY-5-Q-2H-imidazo[4,5-b]pyridin-2-ones and -2-thiones and pharmaceutically-acceptable acid-addition salts thereof, which are useful as cardiotonic agents, where $R_1$, $R_3$, PY and Q are defined hereinbelow.

The invention in a process aspect comprises reacting a 2-$R_3$NH-3-$R_1$NH-5-PY-6-Q-pyridine with urea or carbonyldiimidazole to produce 1,3-dihydro-1-$R_1$-3-$R_3$-6-PY-5-Q-2H-imidazo[4,5-b]pyridin-2-one or with an alkali metal lower-alkyl xanthate, thiourea or thiocarbonyldiimidazole to produce 1,3-dihydro-1-$R_1$-3-$R_3$-6-PY-5-Q-2H-imidazo[4,5-b]pyridine-2-thione.

A composition aspect of the invention relates to a cardiotonic composition for increasing cardiac contractility in a patient, said composition comprising a pharmaceutically-acceptable carrier and, as the active ingredient thereof, an effective amount of a cardiotonic 1,3-dihydro-1-$R_1$-3-$R_3$-6-PY-5-Q-2H-imidazo[4,5-b]pyridin-2-one or -2-thione or pharmaceutically acceptable acid-addition salt thereof.

In a method aspect, the invention relates to a method for increasing cardiac contractility in a patient requiring such treatment which comprises the administration of a medicament comprising a pharmaceutically-acceptable carrier and, as the active component, thereof, an effective amount of the cardiotonic 1,3-dihydro-1-$R_1$-3-$R_3$-6-PY-5-Q-2H-imidazo[4,5-b]pyridin-2-one or -2-thione or pharmaceutically-acceptable acid-addition salt thereof.

DETAILED DESCRIPTION INCLUSIVE OF PREFERRED EMBODIMENTS

In a composition of matter aspect the invention resides in a 1,3-dihydro-1-$R_1$-3-$R_3$-6-PY-5-Q-2H-imidazo[4,5-b]pyridin-2-one or -2-thione having formula I

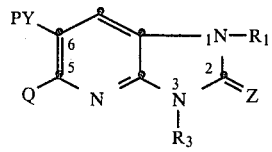

where Z is O or S, Q is hydrogen or lower-alkyl $R_1$ and $R_3$ each are hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, at least one of $R_1$ or $R_3$ being hydrogen, and PY is 4- or 3-pyridinyl or 4- or 3-pyridinyl having one or two lower-alkyl substituents, or pharmaceutically-acceptable acid-addition salts thereof. The compounds of formula I are useful as cardiotonic agents, as determined by standard pharmacological evaluation procedures. Preferred embodiments are those of formula I where PY is 4-pyridinyl or 3-pyridinyl, Z is O, $R_1$ is hydrogen when $R_3$ is methyl, ethyl or 2-hydroxyethyl, and $R_3$ is hydrogen when $R_1$ is methyl, ethyl or 2-hydroxyethyl, and Q is hydrogen, methyl or ethyl. Particularly preferred embodiments are the compounds of formula I where Z is O, $R_1$ is hydrogen, $R_3$ is 2-hydroxyethyl, PY is 4-pyridinyl and Q is hydrogen, methyl or ethyl.

The compound of formula I may exist in tautomeric forms, that is, when $R_1$ is hydrogen as 1,3-dihydro-3-$R_3$-6-PY-5-Q-2H-imidazo[4,5-b]pyridin-2-one or -2-thione of formula I and/or 3-$R_3$-6-PY-5-Q-3H-imidazo[4,5-b]pyridine-2-ol or -2-thiol of formula IA, illustrated as follows

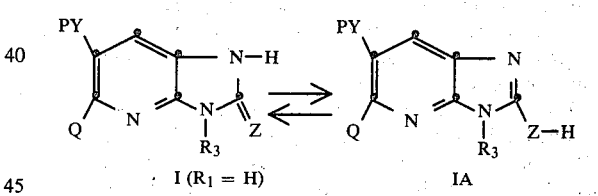

or when $R_3$ is hydrogen as 1,3-dihydro-1-$R_1$-6-PY-5-Q-2H-imidazo[4,5-b]pyridin-2-one or -2-thione of formula I and/or 1-$R_1$-6-PY-5-Q-1H-imidazo[4,5-b]pyridine-2-ol or -2-thiol of formula IB, illustrated as follows

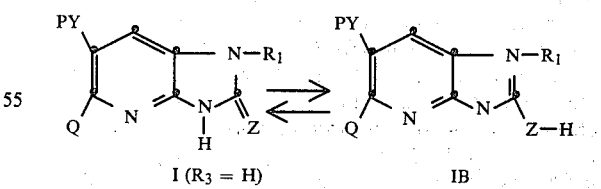

Structural preferences for other known imidazo[4,5-b]pyridin-2-ones or -2-thiones would indicate the above formula I to be the preferred tautomeric structure; thus, we have preferred to use the names based on structure I, although it is understood that in either above instance where $R_1$ or $R_3$ is hydrogen that either or both structures are comprehended herein.

In a process aspect the invention resides in the process of producing the 1,3-dihydro-1-$R_1$-3-$R_3$-6-PY-5-Q-

2H-imidazo[4,5-b]pyridin-2-one or -2-thione of formula I which comprises reacting 2-$R_3$NH-3-$R_1$NH-5-PY-6-Q-pyridine (II) with urea or carbonyldiimidazole to produce the 2-one (I where Z is O) or with an alkali metal xanthate, thiourea or thiocarbonyldiimidazole to produce the 2-thione (I where Z is S), where PY, $R_1$, $R_3$, Z and Q have the meanings given above for the compound of formula I. Preferred embodiments of this process are those which produce the above-said preferred composition embodiments of formula I.

A composition aspect of the invention resides in a cardiotonic composition for increasing cardiac contractility, said composition comprising a pharmaceutically-acceptable carrier and, as the active component thereof, an effective amount of a cardiotonic 1,3-dihydro-1-$R_1$-3-$R_3$-6-PY-5-Q-2H-imidazo[4,5-b]pyridin-2-one (I where Z is O) or 2-thione (I where Z is S) of formula I, where Z, $R_1$, $R_3$, PY and Q are each defined as in formula I, or pharmaceutically-acceptable acid-addition salt thereof. Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient an effective amount of a cardiotonic 1,3-dihydro-1-$R_1$-3-$R_3$-6-PY-5-Q-2H-imidazo[4,5-b]pyridin-2-one (I where Z is O) or -2-thione (I where Z is S) of formula I where PY, $R_1$, $R_3$ and Z are defined as in formula I, or pharmaceutically-acceptable acid-addition salts thereof. Preferred embodiments of this method aspect are those using the preferred cardiotonics of formula I noted above.

The term "lower-alkyl" as used herein, e.g., as one of the meanings for $R_1$, $R_3$ or Q or as a substituent for PY in formula I, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY in formula I where PY is 4-, 3- or 2-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl" as used herein, e.g., for one of the meanings for $R_1$ or $R_3$ in formula I, means hydroxy-alkyl radicals having from two to six carbon atoms which can be arranged as straight or branched chains and at least two carbon atoms of which separate hydroxy and the 1-ring or 3-ring nitrogen atom of the imidazo[4,5-b]pyridine ring, illustrated by 2-hydroxyethyl, 3-hydroxypropyl, 2-hydroxypropyl, 4-hydroxybutyl, 3-hydroxybutyl, 5-hydroxyamyl, 6-hydroxyhexyl, and the like.

The term "lower-alkoxyalkyl" as used herein, e.g., for one of the meanings for $R_1$ or $R_3$ in formula I, means alkoxyalkyl radicals having means from three to six carbon atoms which can be arranged as straight or branched chains and at least two carbon atoms of which separate the oxygen atom of alkoxyalkyl and the 1-ring or 3-ring nitrogen atom of the imidazo[4,5-b]pyridine ring, illustrated by 2-methoxyethyl, 2-ethoxyethyl, 3-methoxypropyl, 2-methoxypropyl, 2-methoxybutyl, 4-ethoxybutyl, 3-ethoxypropyl, 3-n-propoxypropyl, and the like.

The term lower-alkylene designated as Y as part of $R_1$ or $R_3$ herein means lower-alkylene radicals having at least two carbon atoms between its connecting linkages and having from two to six carbon atoms which can be arranged as branched or straight chains, illustrated by —$CH_2CH_2$—, —$CH_2\overset{|}{C}H(CH_3)$, —$CH(CH_3)CH_2$—, —$CH(CH_3)\overset{|}{C}H(CH_3)$, —$\overset{|}{C}HCHCH_2CH_3$,

—$(CH_2)_3$—, —$(CH_2)_4$—, —$(CH_2)_5$—, —$(CH_2)_6$—,

—$CH(C_2H_5)\overset{|}{C}H(CH_3)$, and the like.

The compounds of formula I are useful both in the free base form and in the form of acid-addition salts, and, both forms are within the purview of the invention. The acid-addition salts are simply a more convenient form for use; and in practice, use of the salt form inherently amounts of use of the base form. The acids which can be used to prepare the acid-addition salts include preferably those which produce, when combined with the free base, pharmaceutically-acceptable salts, that is, salt whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form or the hydrochloride salt; however, appropriate pharmaceutically-acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, methanesulfonate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elementary analysis.

The manner of making and using the instant invention will now be generally described so as to enable a person skilled in the art of pharmaceutical chemistry to make and use the same, as follows.

The preparation of 1,3-dihydro-1-$R_1$-3-$R_3$-6-PY-5-Q-2H-imidazo[4,5-b]pyridin-2-one (I, Z is O) by reacting 2-$R_3$NH-3-$R_1$NH-5-PY-6-Q-pyridine (II) with urea is conveniently and preferably carried out by heating the reactants in refluxing dimethylformamide. Alternatively, other suitable inert solvents can be used, e.g., dioxane, nitrobenzene, etc. The reaction using carbonyldiimidazole instead of urea is conveniently carried out in dimethylformamide at about 35° C. for about one to three hours and then at about 70° C. to 80° C. for about two to sixteen hours. This preparation is illustrated further hereinbelow in Examples G-1 through G-37.

The preparation of 1,3-dihydro-1-$R_1$-3-$R_3$-6-PY-5-Q-2H-imidazo[4,5-b]pyridin-2-thione (I, Z is S) is carried out by reacting 2-$R_3$NH-3-$R_1$NH-5-PY-6-Q-pyridine (II) with an alkali metal xanthate, thiourea or thiocarbonyldiimidazole. The reaction using an alkali metal xanthate, preferably the sodium or potassium salt, is conveniently run by refluxing the reactants in a mixture of water and a lower-alkanol, preferably aqueous ethanol. The reaction using thiourea is conveniently run by heating the reactants in refluxing dimethylformamide. The reaction using thiocarbonyldiimidazole is conveniently run at room temperature or slightly above in dimethylformamide. This preparation is further illustrated hereinbelow in Examples H-1 through H-11.

The preparation of the intermediate 2-$R_3$NH-3-$R_1$NH-5-PY-6-Q-pyridines (II), which are disclosed and claimed in copending U.S. patent application Ser. No. 135,100 filed Mar. 28, 1980, filed on even date herewith, is presented in the following paragraphs.

The reaction of a 3-nitro-5-PY-6-Q-2(1H)-pyridinone or of a 5-PY-6-Q-2(1H)-pyridinone with an inorganic halogenating agent to produce a 2-halo-3-nitro-5-PY-6-Q-pyridine (III) or 2-halo-5-PY-6-Q-pyridine (VII) is preferably carried out by refluxing the 2(1H)-pyridinone with excess phosphorus oxychloride containing a catalytic amount of dimethylformamide to obtain the 2-chloro compound. Other suitable inorganic halogenating agents include $PCl_3$, $POBr_3$, $PBr_3$, $PCl_5$, and the like. This reaction is further illustrated below in Examples A-1 through A-17 and B-1 through B-17.

The reaction of the 2-halo compound (III or VII) with ammonia or an amine of the formula $R_3$NH to obtain V or VIII respectively, is run by heating the reactants, preferably under pressure using ammonia or source thereof and monomethylamine and at atmospheric pressure using the other higher primary amines, $R_3NH_2$ or secondary amines, $R_3$RNH. The reaction of III or VII with hydrazine is similarly run to obtain the corresponding 2-hydrazino derivatives, which are readily converted by reduction to the corresponding 2-amines. This reaction is further illustrated hereinbelow in Examples C-1 through C-29 and D-1 through D-9.

The reaction of V to obtain II where $R_1$ is hydrogen is preferably carried out by catalytic hydrogenation of V using a suitable catalyst, e.g., 10% palladium-on-charcoal, Raney nickel, and the like. This reaction is further illustrated hereinbelow in Examples F-1 through F-30.

The reaction of VIII with a halogenating agent to produce the corresponding 3-halo compound (IX) is preferably carried out using bromine to obtain the 3-bromo compound or phenylphosphoric dichloride to obtain the 3-chloro compound. Optionally, the 3-chloro compound (IX) can be obtained in two steps by first reacting 3-nitro-5-PY-6-Q-2(1H)-pyridinone with phenylphosphoric dichloride to produce 2,3-dichloro-5-PY-6-Q-pyridine and then selectively reacting the latter at the more reactive 2-chloro with $R_3$RNH to produce IX. This reaction is further illustrated hereinbelow in Examples E-1 through E-3.

The reaction of IX with ammonia or an amine of the formula $R_1R'NH$ to produce II is carried out by heating the reactants as described above in the conversion of III to V or VII to VIII. This reaction is further illustrated below in Examples F-31 through F-41.

The preparation of the known 1,2-dihydro-2-oxo-5-PY-nicotinic acids by hydrolysis of the corresponding 1,2-dihydro-2-oxo-5-PY-nicotinonitrile is shown in Lesher and Opalka U.S. Pat. No. 4,004,012, issued Jan. 18, 1977.

The hydrolysis of 1,2-dihydro-6-(lower-alkyl)-2-oxo-5-PY-nicotinonitrile to produce 1,2-dihydro-6-(lower-alkyl)-2-oxo-5-PY-nicotinic acid is conveniently run by heating the nitrile on a steam bath with an aqueous mineral acid, e.g., 50% sulfuric acid. This reaction is further illustrated below in Examples K-1 through K-11.

The preparation of the intermediate 1,2-dihydro-2-oxo-5-PY-6-(lower-alkyl)-nicotinonitriles are prepared by the procedure described in the following three paragraphs; this subject matter is disclosed and claimed in copending U.S. patent application Ser. No. 92,504, filed Nov. 26, 1979.

The preparation of 1-PY-2-(dimethylamino)ethenyl lower-alkyl ketone by reacting PY-methyl lower-alkyl ketone with dimethylformamide di-(lower-alkyl) acetal is carried out by mixing the reactants in the presence or absence of a suitable solvent. The reaction is conveniently run at room temperature, i.e., about 20°–25° C., or by warming the reactants up to about 100° C., preferably in a aprotic solvent, conveniently hexamethylphosphoramide because of the method used to prepare the PY-methyl lower-alkyl ketone, as noted below in Example C-1. Other suitable solvents include tetrahydrofuran, dimethylformamide, acetonitrile, ether, benzene, dioxane, and the like. Also the reaction can be run using no solvent, preferably using an excess of dimethylformamide di-(lower-alkyl)acetal. This reaction is further illustrated hereinbelow in Examples I-1 through I-11.

The intermediate PY-methyl lower-alkyl ketones are generally known compounds which are prepared by known methods [e.g., as given in Rec. trav. chim 72, 522 (1953); U.S. Pat. No. 3,133,077 (5-12-64); Bull. Soc. Chim. France 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone with α-cyanoacetamide to produce 1,2-dihydro-2-oxo-5-PY-6-R-nicotinotrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively, however, a longer heating period is required. Other basic condensing agents and solvents include sodium hydride, lithium diethylamide, lithium diisopropylamide, and the like, in an aprotic solvent, e.g., tetrahydrofuran, acetonitrile, ethenyl, benzene, dioxane, and the like. This reaction is further illustrated hereinbelow in Examples J-1 through J-11.

The preparation of the intermediate 6-(lower-alkyl-3-nitro-5-PY-2(1H)-pyridinones is carried out following the procedure described in Example C-1 of U.S. Pat. No. 4,072,746 using in place of 1,2-dihydro-2-oxo-5-(4-pyridinyl)nicotinic acid a molar equivalent quantity of the appropriate 1,2-dihydro-2-oxo-5-PY-6-(lower-alkyl)nicotinic to produce instead of 3-nitro-5-(4-pyridinyl)-2(1H)-pyridinone the corresponding 6-(lower-alkyl)-3-nitro-5-PY-2(1H)pyridinone. This procedure is further illustrated hereinbelow in Example L-1 through L-11.

The preparation of the intermediate 6-(lower-alkyl)-5-PY-2(1H)-pyridinones is carried out following the alternative procedure described from line 59 of column 15 to line 2 of column 16 in Example C-1 of U.S. Pat. No. 4,072,746 using in place of 1,2-dihydro-2-oxo-5-(4-pyridinyl)nicotinonitrile a molar equivalent quantity of the appropriate 1,2-dihydro-2-oxo-5-PY-6-(lower-alkyl)nicotinonitrile to produce instead of 5-(4-pyridinyl)-2(1H)-pyridinone the corresponding 6-(lower-alkyl)-5-PY-2(1H)-pyridinone. This procedure is further illustrated hereinbelow in Examples M-1 through M-11.

The following examples will further illustrate the invention without, however, limiting it thereto.

A. 2-HALO-3-NITRO-5-PY-6-Q-PYRIDINES

A-1. 2-Halo-3-nitro-5-(4-pyridinyl)pyridine, alternatively named 6-chloro-5-nitro-[3,4'-bipyridine]—A mixture containing 108.5 g. of 3-nitro-5-(4-pyridinyl)-2-(1H)-pyridinone, 1250 ml. of phosphorus oxychloride and five drops of dimethylformamide was refluxed for two hours and then allowed to stand at room temperature overnight. The excess phosphorus oxychloride was distilled off in vacuo and the remaining material was poured into ice and water. The aqueous mixture was basified with ammonium hydroxide and stirred for one hour. The solid was collected and dried to yield 102 g. of 2-halo-3-nitro-5-(4-pyridinyl)pyridine.

Following the procedure of Example A-1 but using in place of 3-nitro-5-(4-pyridinyl)-2(1H)-pyridinone a molar equivalent quantity of the appropriate 3-nitro-5-PY-6-Q-2(1H)-pyridinone (preparation of these compounds where Q is lower-alkyl is given hereinbelow in Examples L-1 through L-11, it is contemplated that the corresponding 2-chloro-3-nitro-5-PY-6-Q-pyridines of Examples A-2 through A-16 can be obtained.

A-2. 2-Chloro-3-nitro-5-(3-pyridinyl)pyridine.
A-3. 2-Chloro-3-nitro-5-(2-methyl-3-pyridinyl)-pyridine.
A-4. 2-Chloro-3-nitro-5-(5-methyl-3-pyridinyl)-pyridine.
A-5. 2-Chloro-3-nitro-5-(3-ethyl-4-pyridinyl)-pyridine.
A-6. 2-Chloro-6-methyl-3-nitro-5-(4-pyridinyl)-pyridine.
A-7. 2-Chloro-6-ethyl-3-nitro-5-(4-pyridinyl)-pyridine.
A-8. 2-Chloro-6-methyl-3-nitro-5-(3-pyridinyl)-pyridine.
A-9. 2-Chloro-3-nitro-6-n-propyl-5-(4-pyridinyl)-pyridine.
A-10. 2-Chloro-3-nitro-6-isopropyl-5-(4-pyridinyl)-pyridine.
A-11. 6-n-Butyl-2-chloro-3-nitro-5-(4-pyridinyl)-pyridine.
A-12. 2-Chloro-6-isobutyl-3-nitro-5-(4-pyridinyl)-pyridine.
A-13. 2-Chloro-3-nitro-5-(4-pyridinyl)-6-tert.-butyl-pyridine.
A-14. 2-Chloro-3-nitro-5-n-pentyl-5-(4-pyridinyl)-pyridine.
A-15. 2-Chloro-6-ethyl-5-(2-methyl-4-pyridinyl)-3-nitropyridine.
A-16. 2-Chloro-6-ethyl-3-nitro-5-(3-pyridinyl)-pyridine.

Following the procedure of Example A-1 but using in place of phosphorus oxychloride a molar equivalent quantity of phosphorus oxybromide or phosphorus tribromide, it is contemplated that the compound of Example A-17 can be obtained.

A-17. 2-Bromo-3-nitro-5-(4-pyridinyl)pyridine.

B. 2-HALO-5-PY-6-Q-PYRIDINES

B-1. 2-Chloro-5-(4-pyridinyl)pyridine, alternatively named 6-chloro-[3,4'-bipyridine]—A mixture containing 105 g. of 5-(4-pyridinyl)-2(1H)-pyridinone and 1 liter of phosphorus oxychloride was heated on a steam bath for two hours and then allowed to stand at room temperature overnight. The excess phosphorus oxychloride was distilled off in vacuo and the remaining material poured into ice. The aqueous mixture was made weakly basic with ammonium hydroxide. The precipitate was collected, washed with water and dried in vacuo at 70° C. to yield 108 g. of 2-chloro-5-(4-pyridinyl)-pyridine.

Following the above procedure but using in place of phosphorus oxychloride a molar equivalent quantity of phosphorus oxybromide or phosphorus tribromide, it is contemplated that the corresponding compound of Example B-2 can be obtained.

B-2. 2-Bromo-5-(4-pyridinyl)pyridine.

Following the procedure described in Example B-1 but using in place of 5-(4-pyridinyl)-2(1H)pyridinone a molar equivalent quantity of the corresponding 5-PY-6-Q-2(1H)-pyridinone (preparation of these compounds where Q is lower-alkyl is given hereinbelow in Examples M-1 through M-11), it is contemplated that the corresponding 2-chloro-5-PY-6-Q-pyridines of Examples B-3 through B-17 can be obtained.

B-3. 2-Chloro-5-(3-pyridinyl)pyridine.
B-4. 2-Chloro-5-(2-methyl-3-pyridinyl)pyridine.
B-5. 2-Chloro-5-(5-methyl-3-pyridinyl)pyridine.
B-6. 2-Chloro-5-(3-ethyl-4-pyridinyl)pyridine.
B-7. 2-Chloro-6-methyl-5-(4-pyridinyl)pyridine.
B-8. 2-Chloro-6-ethyl-5-(4-pyridinyl)pyridine.
B-9. 2-Chloro-6-methyl-5-(4-pyridinyl)pyridine.
B-10. 2-Chloro-6-n-propyl-5-(4-pyridinyl)pyridine.
B-11. 2-Chloro-6-isopropyl-5-(4-pyridinyl)pyridine.
B-12. 6-n-Butyl-2-chloro-5-(4-pyridinyl)pyridine.
B-13. 2-Chloro-6-isobutyl-5-(4-pyridinyl)pyridine.
B-14. 2-Chloro-5-(4-pyridinyl)-6-tert.-butylpyridine.

B-15. 2-Chloro-6-n-pentyl-5-(4-pyridinyl)pyridine.
B-16. 2-Chloro-6-ethyl-5-(2-methyl-4-pyridinyl)-pyridine.
B-17. 2-Chloro-6-ethyl-5-(3-pyridinyl)pyridine.

C. 3-NITRO-5-PY-6-Q-PYRIDIN-2-AMINES

C-1. 3-Nitro-5-(pyridinyl)pyridin-2-amine, alternatively named 5-nitro-[3,4'-bipyridin]-6-amine—A mixture containing 27 g. of 2-chloro-3-nitro-5-(4-pyridinyl)-pyridine and 600 ml. of ammonium hydroxide was autoclaved at 100° C. and 150 p.s.i. for eight hours. The solid was collected and dried in vacuo at 70° C. The filtrate was concentrated in vacuo to about 200 ml. and cooled; the separated solid was collected and dried in vacuo at 70° C. The solids were combined, recrystallized twice from dimethylformamide, washed successively with ethanol and ether and dried in vacuo at 70° C. to yield 15 g. of 3-nitro-5-(4-pyridinyl)pyridin-2-amine, m.p. 247°–249° C. with decomposition.

Optionally, the corresponding 3-nitro-5-(4-pyridinyl)pyridine-2-hydrazine was prepared as follows: A mixture containing 10 g. of 2-chloro-3-nitro-5-(4-pyridinyl)pyridine, 50 ml. of hydrazine hydrate and 50 ml. of ethanol was refluxed for one hour and the ethanol and excess hydrazine-hydrate distilled off in vacuo. The residue was dissolved in water and reprecipitated with isopropyl alcohol, collected, washed with isopropyl alcohol and dried in vacuo at 70° C. to yield 7 g. of 3-nitro-5-(4-pyridinyl)pyridin-2-hydrazine.

C-2. N-Methyl-3-nitro-5-(4-pyridinyl)pyridine-2-amine, alternatively named N-methyl-5-nitro-[3,4'-bipyridin]-6-amine—A mixture containing 47 g. of 2-chloro-3-nitro-5-(4-pyridinyl)pyridine, 300 ml. of 40% aqueous methylamine and 300 ml. of ethanol was autoclaved for six hours at 100° C. The solid was filtered off and the filtrate was concentrated in vacuo to a volume of about 200 ml. and then cooled. About 2 g. of dark solid was filtered off and the filtrate was heated in vacuo to dryness. The residue was dissolved in about 250 ml. of water and the aqueous solution was extracted with several portions of chloroform. the chloroform extracts were combined, back-washed with water, dried over anhydrous sodium sulfate, treated with decolorizing charcoal and filtered. The filtrate was stripped in vacuo to yield, as a dark oil, 18.5 g. of N-methyl-3-nitro-5-(4-pyridinyl)-2-pyridine-2-amine.

C-3. N-Ethyl-3-nitro-5-(4-pyridinyl)pyridin-2-amine, alternatively named N-ethyl-5-nitro-[3,4'-bipyridin]-6-amine—A mixture containing 23.56 g. of 2-chloro-3-nitro-5-(4-pyridinyl)pyridine, 80.5 ml. of 70% aqueous ethylamine and 1 liter of 95% ethanol was heated with stirring on a steam bath for over sixteen hours and then concentrated in vacuo to remove solvent and excess aqueous ethylamine. The residue was recrystallized from isopropyl alcohol (final volume of 200 ml.) and dried in a vacuum oven at 60° C. for sixteen hours to yield 16.27 g. of N-ethyl-3-nitro-5-(4-pyridinyl)pyridin-2-amine, m.p. 129°–132° C.

C-4. N-(2-Hydroxyethyl)-3-nitro-5-(4-pyridinyl)-pyridin-2-amine, alternatively named N-(2-hydroxyethyl)-5-nitro-[3,4'-bipyridin]-6-amine—A mixture containing 23.56 g. of 2-chloro-3-nitro-5-(4-pyridinyl)pyridine, 63.0 ml. of 2-aminoethanol and 1000 ml. of ethanol was refluxed with stirring over sixteen hours and the filtrate concentrated to one-half of its volume in vacuo. The separated solid was collected to yield 13 g. of orange-brown solid. The filtrate was concentrated in vacuo to less than 200 ml. and was diluted with water. The resulting precipitate was collected to yield another 7 g. of brown solid which was recrystallized from isopropyl alcohol to yield orange-brown prisms; this orange-brown material was combined with the above 13 g. of orange-brown solid and the combined material was recrystallized from isopropyl alcohol (600 ml. final volume) to yield, as an orange-brown solid, 12.42 g. of N-(2-hydroxyethyl)-3-nitro-5-(4-pyridinyl)pyridin-2-amine, m.p. 188°–190° C. after sintering about 180° C. Concentration of the filtrate to about 250 ml. yielded additional orange-brown solid, which was collected, dried and found to melt at 183°–186° C.

C-5. N-(2-Dimethylaminoethyl)-3-nitro-5-(4-pyridinyl)pyridin-2-amine, alternatively named N-(2-dimethylaminoethyl)-5-nitro-[3,4'-bipyridin]-6-amine—A mixture containing 11.77 g. of 2-chloro-3-nitro-5-(4-pyridinyl)-pyridine, 8.6 ml. of 2-dimethylaminoethylamine and 500 ml. of ethanol was refluxed with stirring over twenty-two hours, the hot solution filtered and the filtrate concentrated in vacuo to remove the solvent. The residue was recrystallized from 1000 ml. of cyclohexane to yield some insoluble brown oil, 5.6 g. of yellow solid N-(2-dimethylaminoethyl)-3-nitro-5-(4-pyridinyl)pyridin-2-amine, m.p. 110°–112° C., and from the filtrate, another 1.2 g. of yellow solid product, m.p. 110°–112° C., sintering at 107° C. The insoluble brown oil was taken up in methanol and was concentrated several times with cyclohexane; the insoluble material was filtered off and the filtrate concentrated to less than 300 ml. Some insoluble brown gum was filtered off and the filtrate on cooling yielded another 2.14 g. of yellow solid product, m.p. 109°–111° C.

C-6. N-(2-Diethylaminoethyl)-3-nitro-5-(4-pyridinyl)pyridin-2-amine, alternatively named N-(2-diethylaminoethyl)-5-nitro-[3,4'-bipyridin]-6-amine—A mixture containing 47.13 g. of 2-chloro-3-nitro-5-(4-pyridinyl)pyridine, 70.8 ml. of 2-diethylaminoethylamine and 1.4 liters of ethanol was refluxed with stirring for over four hours. The ethanolic solution of the reaction mixture was filtered through diatomaceous earth (no insoluble material) and the filtrate was diluted with 2 liters of water and the resulting aqueous mixture chilled. The precipitated yellow-orange solid was collected and dried in vacuo at 90° C. for over sixteen hours to yield 43.2 g. of orange-yellow solid N-(2-diethylaminoethyl)-3-nitro-5-(4-pyridinyl)pyridin-2-amine, m.p. 100.5°–102° C., after sintering at 100° C. Another 1.75 g. of yellow-orange solid product, m.p. 100°–101° C., after sintering at 99° C., was obtained from the filtrate.

C-7. N-(3-Dimethylaminopropyl)-3-nitro-5-(4-pyridinyl)pyridin-2-amine—A mixture containing 47.13 g. of 2-chloro-3-nitro-5-(4-pyridinyl)pyridine, 63.6 ml. of 3-dimethylaminopropylamine and 700 ml. of ethanol was refluxed with stirring for over five hours and then allowed to stand overnight at room temperature. The solution was then concentrated in vacuo to a volume of about 250 ml. and the resulting concentrated solution was diluted with 800 ml. of water. The separated solid was collected and dried in vacuo at 90° C. for over sixty hours to yield 49.4 g. of orange-brown solid, m.p. 94°–96° C., after sintering about 80° C. The solid was dissolved in about 250 ml. of methanol and the hot solution diluted with water and cooled. The separated yellow solid was air-dried for over forty-eight hours, to yield 45.5 g. of N-(3-dimethylaminopropyl)-3-nitro-5-

(4-pyridinyl)pyridin-2-amine, m.p. 95.6° C., after softening at 90° C. and sintering at 94° C.

C-8. N,N-Dimethyl-3-nitro-5-(4-pyridinyl)pyridin-2-amine—A mixture containing 25.92 g. of 2-chloro-3-nitro-5-(4-pyridinyl)pyridine, 62 g. of 40% aqueous dimethylamine and 600 ml. of 95% ethanol was autoclaved at 100° C. for over eight hours. The solvent was distilled off in vacuo and the remaining yellow solid residue was recrystallized from isopropyl alcohol (300 ml.)-water to yield, after drying at 90° C. in vacuo over potassium hydroxide for sixteen hours, 24.46 g. of N,N-dimethyl-3-nitro-5-(4-pyridinyl)pyridin-2-amine, m.p. 135°–137° C.

C-9. N-[2-(4-Morpholinyl)ethyl]-3-nitro-5-(4-pyridinyl)pyridin-2-amine—A mixture containing 30.48 g. of 2-chloro-3-nitro-5-(4-pyridinyl)pyridine, 33.7 g. of 97% 2-(4-morpholinyl)ethylamine and 450 ml. of ethanol was refluxed with stirring for over five hours and the reaction mixture allowed to cool. The separated product was collected and dried in vacuo over four hours at 90° C. to yield 36.0 g. of N-[2-(4-morpholinyl)ethyl]-3-nitro-5-(4-pyridinyl)pyridin-2-amine, m.p. 140°–141° C., after sintering at 139° C. Another 3.73 g. of product, m.p. 134°–136° C. after sintering at 133° C. was obtained by concentrating the filtrate to a volume of about 100 ml., adding water, filtering the precipitate and drying it as above.

Following the procedure described in Example C-1 or C-3 but using in place of 2-chloro-3-nitro-5-(4-pyridinyl)pyridine and ammonium hydroxide or ethylamine corresponding molar equivalent quantities respectively of the appropriate 3-nitro-5-PY-6-Q-pyridine and ammonium hydroxide, $R_3NH_2$ or RRNH, it is contemplated that the 3-nitro-5-PY-6-Q-pyridin-2-amines of Examples C-10 through C-29 can be obtained.

C-10. N-n-Propyl-3-nitro-5-(3-pyridinyl)pyridine-2-amine.

C-11. N-Isopropyl-3-nitro-5-(2-methyl-5-pyridinyl)-pyridin-2-amine.

C-12. N-n-Butyl-3-nitro-5-(5-methyl-3-pyridinyl)-pyridin-2-amine.

C-13. N-n-Amyl-3-nitro-5-(4-pyridinyl)pyridin-2-amine.

C-14. N-n-Hexyl-3-nitro-5-(3-pyridinyl)pyridin-2-amine.

C-15. N-Ethyl-5-methyl-3-nitro-5-(4-pyridinyl)-pyridin-2-amine.

C-16. N,N-Diethyl-6-ethyl-3-nitro-5-(4-pyridinyl)-pyridin-2-amine.

C-17. N,N-Dimethyl-6-methyl-3-nitro-5-(3-pyridinyl)pyridin-2-amine.

C-18. 3-Nitro-5-n-propyl-5-(4-pyridinyl)pyridin-2-amine.

C-19. 3-Nitro-6-isopropyl-5-(4-pyridinyl)pyridin-2-amine.

C-20. 6-n-Butyl-3-nitro-5-(4-pyridinyl)pyridin-2-amine.

C-21. 6-Isobutyl-3-nitro-5-(4-pyridinyl)pyridine-2-amine.

C-22. 3-Nitro-5-(4-pyridinyl)-6-tert.-butylpyridin-2-amine.

C-23. 3-Nitro-6-n-pentyl-5-(4-pyridinyl)pyridin-2-amine.

C-24. N-(2-Ethoxyethyl)-6-ethyl-5-(2-methyl-4-pyridinyl)-3-nitropyridin-2-amine.

C-25. N-(2-Methoxyethyl)-6-ethyl-3-nitro-5-(3-pyridinyl)pyridin-2-amine.

C-26. N-(3-Methoxypropyl)-3-nitro-5-(4-pyridinyl)-pyridin-2-amine.

C-27. N-(2-Hydroxyethyl)-3-nitro-5-(4-pyridinyl)-pyridin-2-amine.

C-28. N-(3-Hydroxypropyl)-3-nitro-5-(4-pyridinyl)-pyridin-2-amine.

C-29. N-(2,3-Dihydroxypropyl)-3-nitro-5-(4-pyridinyl)pyridin-2-amine.

D. 5-PY-6-Q-PYRIDIN-2-AMINES

D-1. 5-(4-Pyridinyl)pyridin-2-amine, alternatively named [3,4'-bipyridin]-6-amine—A mixture containing 48 g. of 2-chloro-5-(4-pyridinyl)pyridine and 700 ml. of ammonium hydroxide was heated in an autoclave at 150° C. and 200 p.s.i. for sixteen hours. The solid was collected, washed with water and dried. The filtrate was distilled in vacuo to remove the excess ammonium hydroxide and the remaining residue was combined with the above solid and the combined material was recrystallized from water and dried in vacuo at 70° C. to yield 29 g. of 5-(4-pyridinyl)pyridin-2-amine, m.p. 192°–195° C.

D-2. N-Methyl-5-(4-pyridinyl)pyridin-2-amine—A mixture containing 52 g. of 2-chloro-5-(4-pyridinyl)-pyridine and 250 ml. of 40% aqueous methylamine was heated in an autoclave at 150° C. and 300 p.s.i. for fifteen hours. The reaction mixture ws then distilled in vacuo to remove the excess water and methylamine and the residue was slurried up in water. The solid was collected, washed with water and dried and then recrystallized from acetonitrile, washed with ether and dried in vacuo at 70° C. to yield 25 g. of N-methyl-5-(4-pyridinyl)pyridin-2-amine, m.p. 152°–154° C.

D-3. N,N-Dimethyl-5-(4-pyridinyl)pyridin-2-amine—A mixture containing 25 g., of 2-chloro-5-(4-pyridinyl)pyridine and 110 ml. of 40% aqueous dimethylamine was autoclaved at 150° C. and 100 p.s.i. for fifteen hours. The solid was collected, washed with water, dried, recrystallized from 50% aqueous ethanol, dried in vacuo at 70° C. to yield 18.5 g. of N,N-dimethyl-5-(4-pyridinyl)pyridin-2-amine, m.p. 176°–178° C.

Following the procedure described in Example D-2 but using in place of methylamine a molar equivalent quantity of $R_3NH_2$, it is contemplated that the N-$R_3$-5-(4-pyridinyl)pyridin-2-amines of Examples D-4 through D-9 can be obtained.

D-4. N-Ethyl-5-(4-pyridinyl)pyridin-2-amine.

D-5. N-(n-Propyl)-5-(4-pyridinyl)pyridin-2-amine.

D-6. N-(Isobutyl)-5-(4-pyridinyl)-pyridin-2-amine.

D-7. N-(2-Methoxyethyl)-5-(4-pyridinyl)pyridin-2-amine.

D-8. N-(2-Hydroxyethyl)-5-(4-pyridinyl)pyridin-2-amine.

D-9. N-(2-Dimethylaminoethyl)-5-(4-pyridinyl)pyridin-2-amine.

E. 3-HALO-5-PY-6-Q-PYRIDIN-2-AMINES

E-1. 3-Bromo-5-(4-pyridinyl)pyridin-2-amine, optionally named 5-bromo-[3,4--bipyridin]-6-amine—A solution containing 17 g. of 5-(4-pyridinyl)pyridin-2-amine in 200 ml. of acetic acid warmed to 70° C. was treated dropwise with 17.6 g. of bromine. The reaction mixture was heated at about 70°–75° C. for thirty minutes, allowed to cool and then diluted with ether. The precipitate was collected, washed with ether and dried. The solid was dissolved in water and the aqueous solution was basified with 2 N aqueous potassium hydroxide solution. The precipitate was collected, washed with water and dried and then recrystallized from ethanol and dried in vacuo at 70° C. to yield 14.5 g. of 3-bromo-5-(4-pyridinyl)pyridin-2-amine, m.p. 197° C. A sample for analysis was recrystallized twice from ethanol, the second time using decolorizing charcoal and then washing with ether and drying in vacuo at 70° C. to yield 8 g. of the product, m.p. 198°–199° C.

E-2. N-Methyl-3-bromo-5-(4-pyridinyl)pyridin-2-amine—To a solution containing 9.3 g. of N-methyl-5-(4-pyridinyl)pyridin-2-amine in 100 ml. of acetic acid at room temperature was added dropwise with stirring 8.8 g. of bromine. The reaction mixture was stirred at room temperature for one hour. The solid was collected, washed with ether and dried. The solid was dissolved in water and the aqueous solution was basified with ammonium hydroxide with stirring. The solid was collected, washed with water and dried. The solid was recrystallized from acetonitrile using decolorizing charcoal, washed with ether and dried in vacuo at 70° C. to yield 8 g. of N-methyl-3-bromo-5-(4-pyridinyl)pyridin-2-amine, m.p. 165°–167° C.

E-3. 3-Chloro-5-(4-pyridinyl)pyridin-2-amine—A mixture containing 22 g. of 3-chloro-5-(4-pyridinyl)pyridine-2-hydrazine, 300 ml. of dimethylforamide and 2 g. of Raney nickel in a Parr apparatus was shaken with hydrogen under catalytic hydrogenation conditions for three hours. When a tlc analysis indicated the presence of starting material, another 2 g. of Raney nickel was added and the hydrogenation was continued at 45° C. for four hours. The solvent was distilled off in vacuo and the remaining residue was recrystallized once from methanol and a second time from ethanol using decolorizing charcoal. The solid was dissolved in 6 N hydrogen chloride and isopropyl alcohol was added. The mixture was cooled and the separated product was collected, washed successively with isopropyl alcohol and ether and dried in vacuo at 70° C. to yield 2.5 g. of 3-chloro-5-(4-pyridinyl)pyridin-2-amine dihydrochloride monohydrate, m.p. 283°–286° C.

The above intermediate 3-chloro-5-(4-pyridinyl)pyridine-2-hydrazine was prepared in two steps as follows: A mixture containing 31 g. of 3-nitro-5-(4-pyridinyl)-2(1H)-2-pyridinone, and 150 ml. of phenylphosphonic dichloride was heated on an oil bath at 210°–220° C. for two hours and then allowed to cool. The reaction mixture was poured into ice and water and the aqueous mixture was basified with ammonium hydroxide while stirring. The separated product was collected, washed with water and dried. It was then recrystallized from isopropyl alcohol and dried to yield 17 g. of 2,3-dichloro-5-(4-pyridinyl)pyridine, m.p. 274°–275° C. with decomposition. A mixture containing 9 g. of 2,3-dichloro-5-(4-pyridinyl)pyridine, 50 ml. of 100% hydrazine hydrate and 50 ml. of ethanol was refluxed for one hour and then cooled. The separated hydrazine hydrochloride was filtered off and the filtrate was heated in vacuo to remove the solvent to yield 7 g. of 3-chloro-5-(4-pyridinyl)pyridine-2-hydrazine in free base form. Said free base form was recrystallized from dimethylformamide and then dissolved in 6 N hydrogen chloride and the solution treated with isopropyl alcohol. The mixture was cooled and the separated product was collected, washed with ether and dried in vacuo at 70° C. to yield 5 g. of 3-chloro-5-(4-pyridinyl)pyridine-2-hydrazine dihydrochloride, m.p. 298°–300° C. with decomposition.

F. 2-$R_1$NH-3-$R_3$NH-5-PY-6-Q-PYRIDINES

F-1. 2,3-Diamino-5-(4-pyridinyl)pyridine, alternatively named [3,4'-bipyridin]-5,6-diamine—A mixture containing 7 g. of 3-nitro-5-(4-pyridinyl)pyridine-2-hydrazine, 150 ml. of dimethylformamide and 2 g. of Raney nickel was shaken in a Parr apparatus with hydrogen under pressure at 45° C. for twelve hours. The reaction mixture was filtered and the filtrate heated in vacuo to remove the solvent. The residue was shaken well with water and the solid again collected. The solid was crystallized from ethanol, dissolved in 6 N hydrogen chloride and reprecipitated with ethyl alcohol and the mixture cooled. The product was collected, washed successively with ethanol and ether and dried in vacuo at 70° C. to yield 3 g. of 2,3-diamino-5-(4-pyridinyl)pyridine dihydrochloride, m.p. >300° C.

Alternatively, the above product can be prepared by reducing the corresponding 3-nitro-5-(4-pyridinyl)pyridin-2-amine as follows: a mixture containing 27 g. of 3-nitro-5-(4-pyridinyl)pyridin-2-amine, 200 ml. of dimethylformamide and 2 g. of 10% palladium-on-charcoal was catalytically hydrogenated in a Parr apparatus for three and one-half hours at room temperature. The reaction mixture was filtered and the filtrate heated in vacuo to remove the solvent. The residue was combined with material obtained in another run starting with 10 g. of 3-nitro-5-(4-pyridinyl)pyridin-2-amine and the combined material was recrystallized from ethanol, washed with ether and dried in vacuo at 70° C. to yield 14 g. of 2,3-diamino-5-(4-pyridinyl)pyridine.

F-2. 3-Amino-2-methylamino-5-(4-pyridinyl)pyridine—A mixture containing 21 g. of 2-methylamino-3-nitro-5-(4-pyridinyl)pyridine, 200 ml. of ethanol and 2 g. of 10% palladium-on-charcoal was shaken under catalytic hydrogenation conditions in a Parr apparatus at room temperature for three hours. The reaction mixture was filtered and the solvent distilled off in vacuo. The remaining solid was recrystallized from acetonitrile, washed with ether and dried in vacuo at 70° C. to yield 3-amino-2-methylamino-5-(4-pyridinyl)pyridine (alternatively named $N^6$-methyl-[3,4'-bipyridine]-5,6-diamine), m.p. 184°–187° C.

F-3. 3-Amino-2-ethylamino-5-(4-pyridinyl)pyridine—A mixture containing 18.11 g. of 2-ethylamino-3-nitro-5-(4-pyridinyl)pyridine, 250 ml. of ethanol and 2.0 g. of 10% palladium-on-charcoal was shaken in a Parr apparatus under catalytic hydrogenation conditions for twenty-one hours at room temperature. The reaction mixture was filtered and the filtration was heated in vacuo to remove the solvent. The remaining residue was recrystallized from acetonitrile using decolorizing charcoal (final volume of 300 ml.) and dried at 70° C. in a vacuum oven for sixteen hours to produce 8.55 g. of compound melting at 179°–183° C. A second crop of 4.36 g. of material, m.p. 179°–183° C. was obtained by concentrating the filtrate to 100 ml. A 4.72 g. portion of this product was combined with an 8.37 g. portion of this product was combined with an 8.37 g. portion of product obtained in another run and the combined material was recrystallized from acetonitrile (final volume of 200 ml.) and dried in a vacuum oven at 90° C. over sixty hours to yield a first crop of 7.92 g. of 3-amino-2-ethylamino-5-(4-pyridinyl)pyridine, m.p. 183°–186° C. and a second crop of 3.73 g. of product, m.p. 182°–186° C.

F-4. 3-Amino-2-(2-hydroxyethylamino)-5-(4-pyridinyl)pyridine—A mixture containing 11.93 g. of 2-(2-hydroxyethylamino)-3-nitro-5-(4-pyridinyl)pyridine, 250 ml. of ethanol and 2 g. of 10% palladium-on-charcoal was catalytically hydrogenated by shaking in a Parr apparatus at room temperature for over four hours. The reaction mixture was filtered to remove the catalyst and the filtrate was concentrated in vacuo to remove the solvent. The remaining solid residue was recrystallized from acetonitrile (final volume of 350 ml.) and dried in a vacuum oven at 90° C. for twenty hours to yield 8.45 g. of 3-amino-2-(2-hydroxyethylamino)-5-(4-pyridinyl)pyridine, m.p. 190°–191.5° C.

F-5. 3-Amino-2-(2-dimethylaminoethylamino)-5-(4-pyridinyl)pyridine—A mixture containing 18.26 g. of 2-(2-dimethylaminoethylamino)-3-nitro-5-(4-pyridinyl)pyridine, 250 ml. of ethanol and 2.0 g. of 10% palladium-on-charcoal was hydrogenated by shaking in a Parr apparatus under catalytic hydrogenation conditions for seventy-two minutes at room temperature. The catalyst was filtered off and the filtrate was distilled in vacuo to remove the solvent. The residue was recrystallized from acetonitrile (final volume of 150 ml.) and dried at 70° C. in a vacuum oven over sixty hours to yield 13.4 g. of 3-amino-2-(2-dimethylaminoethylamino)-5-(4-pyridinyl)pyridine, m.p. 138°–141° C.

F-6. 3-Amino-2-(2-diethylaminoethylamino)-5-(4-pyridinyl)pyridine—A mixture containing 13.15 g. of 2-(2-diethylaminoethylamino)-3-nitro-5-(4-pyridinyl)pyridine, 250 ml. of ethanol and 2 g. of 10% palladium-on-charcoal was shaken in a Parr apparatus under catalytic hydrogenation conditions for over one and three-fourth hours at room temperature. The catalyst was filtered off and the filtrate was concentrated in vacuo to remove the solvent. The residue was recrystallized from 300 ml. of cyclohexane and dried at 90° C. in a vacuum oven for sixteen hours to yield 10.11 g. of 3-amino-2-(2-diethylaminoethylamino)-5-(4-pyridinyl)pyridine monohydrate, m.p. 104°–106° C.

F-7. 3-Amino-2-(3-dimethylaminopropylamino)-5-(4-pyridinyl)pyridine—A mixture containing 22.6 g. of 2-(3-dimethylaminopropylamino)-3-nitro-5-(4-pyridinyl)pyridine, 250 ml. of ethanol and 2.0 g. of 10% palladium-on-charcoal was catalytically hydrogenated in a Parr apparatus for one and three-fourth hours at room temperature. The catalyst was filtered off and the filtrate was combined with the corresponding filtrate of an identical run except for a three hour hydrogenation period and the combined filtrates were concentrated in vacuo to remove the solvent. The residue was dissolved in hot acetonitrile (final volume of 200 ml.) and cooled. When no solid separated the acetonitrile solution was diluted to a volume of 500 ml. and this solution was treated with decolorizing charcoal, filtered and the filtrate concentrated to a volume of 200 ml. The resulting solution chilled. The separated product was collected and dried in a vacuum oven at 90° C. for sixteen hours to yield 37 g. of 3-amino-2-(3-dimethylaminopropylamino)-5-(4-pyridinyl)-pyridine, m.p. 137°–138° C.

F-8. 3-Amino-2-dimethylamino-5-(4-pyridinyl)pyridine—A mixture containing 24.43 g. of 2-dimethylamino-3-nitro-5-(4-pyridinyl)pyridine, 250 ml. of ethanol and 2 g. of palladium-on-charcoal was shaken in a Parr apparatus under catalytic hydrogenation conditions for three hours at room temperature. The catalyst was filtered off and the filtrate was distilled in vacuo to remove the solvent. The residue was recrystallized twice from acetonitrile (100 ml. and 250 ml., respectively) and dried at 90° C. in a vacuum oven over sixty hours to yield 10.52 g. of 3-amino-2-dimethyl-amino-5-(4-pyridinyl)pyridine, m.p. 190°–194° C.

F-9. 2-Amino-3-methylamino-5-(4-pyridinyl)-pyridine—A mixture containing 33 g. of 2-amino-3-bromo-5-(4-pyridinyl)pyridine, 700 ml. of 40% aqueous methylamine, a pinch of copper-bronze metal and a pinch of cupric sulfate pentahydrate was autoclaved at 160° C. for sixty hours. The reaction mixture was filtered and the filtrate distilled in vacuo to remove the excess aqueous methylamine. The residue was slurried up in a minimum amount of cold water and the solid collected and dried. The solid was recrystallized twice from dimethylformamide, washed successively with ethanol and ether and dried in vacuo at 70° C. to yield 4 g. of 2-amino-3-methylamino-5-(4-pyridinyl)pyridine, m.p.282°–285° C.

F-10. 3-Amino-2-[2-(4-morpholinyl)ethylamino]-5-(4-pyridinyl)pyridine—A mixture containing 16.34 g. of 2-[2-(4-morpholinyl)ethylamino]-3-nitro-5-(4-pyridinyl)-pyridine, 250 ml. of ethanol and 2 g. of 10% palladium-on-charcoal was shaken in a Parr apparatus under catalytic hydrogenation conditions at room temperature for five hours. The catalyst was filtered off and the filtrate was concentrated in vacuo to remove the solvent. The residue was recrystallized from ethanol (80 ml.)-water and dried at 80° C. in a vacuum oven for eight hours and then redried at 90° C. in a vacuum oven for eighteen hours, to yield 9.79 g. of 3-amino-2-[2-(4-morpholinyl)ethylamino]-5-(4-pyridinyl)-pyridine, m.p. 122°–125° C.

Following the procedure described in Example F-1 or F-2 but using in place of 3-nitro-5-(4-pyridinyl)pyridin-2-amine or N-methyl-3-nitro-5-(4-pyridinyl)pyridin-2-amine a molar equivalent quantity of the appropriate 2-$R_3$NH (or RRN)-3-nitro-5-PY-6-Q-pyridine, it is contemplated that the corresponding 3-amino-2-($R_3$NH or RRN)-5-PY-6-Q-pyridines of Examples F-11 through F-30 can be obtained.

F-11. 3-Amino-2-n-propylamino-5-(3-pyridinyl)-pyridine.

F-12. 3-Amino-2-isopropylamino-5-(2-methyl-5-pyridinyl)pyridine.

F-13. 3-Amino-2-n-butylamino-5-(5-methyl-3-pyridinyl)pyridine.

F-14. 3-Amino-2-n-amylamino-5-(4-pyridinyl)pyridine.

F-15. 3-Amino-2-n-hexylamino-5-(3-pyridinyl)pyridine.

F-16. 3-Amino-6-methyl-5-(4-pyridinyl)pyridine.

F-17. 3-Amino-6-ethyl-2-diethylamino-5-(4-pyridinyl)pyridine.

F-18. 3-Amino-2-dimethylamino-6-methyl-5-(3-pyridinyl)pyridine.

F-19. 3-Amino-6-n-propyl-5-(4-pyridinyl)pyridine.

F-20. 3-Amino-6-isopropyl-5-(4-pyridinyl)pyridine.

F-21. 3-Amino-6-n-butyl-5-(4-pyridinyl)pyridine.

F-22. 3-Amino-6-isobutyl-5-(4-pyridinyl)pyridine.

F-23. 3-Amino-5-(4-pyridinyl)-6-tert.-butylpyridine.

F-24. 3-Amino-6-n-pentyl-5-(4-pyridinyl)pyridine.

F-25. 3-Amino-2-(2-ethoxyethylamino)-6-ethyl-5-(2-methyl-4-pyridinyl)pyridine.

F-26. 3-Amino-6-ethyl-2-(2-methoxyethylamino)-5-(3-pyridinyl)pyridine.

F-27. 3-Amino-2-(3-methoxypropylamino)-5-(4-pyridinyl)pyridine.

F-28. 3-Amino-2-(2-hydroxyethylamino)-6-methyl-5-(4-pyridinyl)pyridine.

F-29. 3-Amino-2-(3-hydroxypropylamino)-5-(4-pyridinyl)pyridine.

F-30. 3-Amino-2-(2,3-dihydroxypropylamino)-5-(4-pyrdinyl)pyridine.

Following the procedure described in Example F-9 but using in place of methylamine a molar equivalent quantity of the appropriate $R_1NH_2$ or $R'R'NH$, it is contemplated that the corresponding 2-amino-3-$R_1NH$(or $R'R'N$)-5-(4-pyridinyl)-pyridines of Examples F-31 through F-40 can be obtained.

F-31. 2-Amino-3-ethylamino-5-(4-pyridinyl)pyridine.

F-32. 2-Amino-3-n-propylamino-5-(4-pyridinyl)pyridine.

F-33. 2-Amino-3-isopropylamino-5-(4-pyridinyl)pyridine.

F-34. 2-Amino-3-n-butylamino-5-(4-pyridinyl)pyridine.

F-35. 2-Amino-3-(2-hydroxyethylamino)-5-(4-pyridinyl)pyridine.

F-36. 2-Amino-3-(2,3-dihydroxypropylamino)-5-(4-pyridinyl)pyridine.

F-37. 2-Amino-3-(3-methoxypropylamino)-5-(4-pyridinyl)pyridine.

F-38. 2-Amino-3-(2-ethoxyethylamino)-5-(4-pyridinyl)pyridne.

F-39. 2-Amino-3-(2-dimethylaminoethylamino)-5-(4-pyridinyl)pyridine.

F-40. 2-Amino-3-(3-diethylaminopropylamino)-5-(4-pyridinyl)pyridine.

F-41. 2-Amino-3-[2-(4-morpholinyl)ethylamino]-5-(4-pyridinyl)pyridine.

G.
1-$R_1$-3-$R_3$-6-PY-5-Q-2H-IMIDAZO[4,5-b]PYRIDIN-3-ONES

G-1. 1,3-Dihydro-6-(4-pyridinyl)-2H-imidazo[4,5-b]pyridin-2one—A mixture containing 20 g. of 2,3-dimaino-5-(4-pyridinyl)pyridine dihydrochloride, 28 g. of urea and 200 ml. of dimethylformamide was refluxed for two hours and then allowed to stand at room temperature overnight. The reaction mixture was poured into a mixture of ice and water and the resulting solid was collected, washed with water and dried. The solid was dissolved in 200 ml. of hot 6 N hydrochloric acid, the solution treated with decolorizing charcoal and filtered, and the filtrate poured into a rapidly stirred liter of ethanol. The resulting mixture was cooled. The separated solid was collected, washed successively with ethanol and ether, and then dried. The solid was then recrystallized from water using decolorizing charcoal, washed successively with ethanol and ether and dried in vacuo at 70° C. to yield 6.5 g. of 1,3-dihydro-6-(4-pyridinyl)-2H-imidazo[4,5-b]pyridin-2- one hydrochloride, m.p. >300° C.

G-2. 1,3-Dihydro-3-methyl-6-(4-pyridinyl)-2H-imidazo)[4,5-b]pyridin-2one—A mixture containing 7 g. of 3-amino-2-methylamino-5-(4-pyridinyl)pyridine, 6 g. of urea and 100 ml. of diethylformamide was refluxed for two hours, cooled and then poured into a mixture of ice and water. The separated solid was collected, washed with water and dried. The solid was recrystallized twice from dimethylformamide, washed successively with ethanol and ether and dried in vacuo at 70° C. to yield 5 g. of 1,3-dihydro-3-methyl-6-(4-pyridinyl)-2H-imidazo[4,5-b]pyridin-2-one, m.p. >300° C.

G-3. 3-Ethyl-1,3-dihydro-6-(4-pyridinyl)-2H-imidazo[4,5-b]pyridin-2-one—A mixture containing 8.57 g. of 3-amino-2-ethylamino-5-(4-pyridinyl)pyridine, 9.73 g. of carbonyldiimidazole and 200 ml. of dimethylformamide was stirred in a water bath at 35° C. for over ninety minutes, at room temperature overnight and then heated to 80° C. for thirty minutes. To the mixture was added 15 ml. of water and the solution was treated with decolorizing charcoal and filtered. The filtrate was concentrated in vacuo to remove the liquid and the residue was recrystallized from acetonitrile (final volume of 140 ml.) and dried at 90° C. in a vacuum oven for sixteen hours to yield 5.15 g. of dark green solid. Another 2.56 g. of green solid had not dissolved in the acetonitrile. The 5.15 g. portion of green solid was recrystallized from ethyl acetate (350 ml.) and dried at 90° C. in a vacuum oven for twenty hours to yield, as pale green prisms, 4.01 g. of 3-ethyl-1,3-dihydro-6-(4-pyridinyl)-2H-imidazo[4,5-b]pyridin-2-one, m.p. 244°-246° C. Also the original 2.56 g. of insoluble green solid was recrystallized from ethyl acetate (150 ml.) and dried at 90° C. in vacuo to yield another 1.5 g. of product. The 4.01 g. and 1.51 g. portions of product were combined and dried in a vacuum oven at 100° C. for over sixty hours to yield 5.38 g. of said product, m.p. 244°-246° C.

G-4. 1,3-Dihydro-3-(2-hydroxyethyl)-6-(4-pyridinyl)-2H-imidazo[4,5-b]pyridin-2-one—A mixture containing 9.04 g. of 3-amino-2-(2-hydroxyethylamino)-5-(4-pyridinyl)-pyridine, 14.61 g. of urea and 300 ml. of dimethylformamide was refluxed with stirring for over twenty hours and the dimethylformamide was distilled off in vacuo. The resulting residue was suspended in water and the solid was collected, recrystallized from isopropyl alcohol (final volume 600 ml.), and dried at 90° C. In a vacuum oven for over sixteen hours to yield 7.84 g. of product and a second portion of 2.18 g. after concentrating the filtrate to a volume of 100 ml. The combined 7.84 g. and 2.18 g. portions of the product were combined and recrystallized from methanol (final volume of 250 ml.) and dried in a vacuum oven at 90° C. for over sixteen hours to yield 6.54 g. of product. A 6.50 g. portion of this product was mixed with 200 ml. of an equimolar mixture of diphenyl and diphenyl ether and the mixture was stirred under reflux for ninety minutes and partially cooled. The resulting suspension was diluted with n-hexane and the tan solid was collected and combined with another 0.95 g. portion of the product prepared in another run by the same procedure and the combined solids were recrystallized from methanol (final volume of 100 ml.) and dried at 90° C. ) in a vacuum oven for over sixty hours to yield, as light-brown prisms, 4.26 g. of 1,3-dihydro-3-(2-hydroxyethyl)-6-(4-pyridinyl)-2H-imidazo[4,5-b]pyridin-2-one, m.p. 283°-284° C. The product was then dissolved in 150 ml. of dimethylformamide and the solution was treated with a slight excess of hydrogen chloride in ethanol, the mixture was diluted with ether, and the resulting solid was collected, dried in a vacuum oven at 85° C. for over sixty hours to yield, as a tan solid, 4.44 g. of 1,3-dihydro-3-(2-hydroxyethyl)-6-(4-pyridinyl)-2H-imidazo-[4,5-b]pyridin-2-one monohydrochloride hemihydrate, m.p. 297°-299° C. with decomposition.

G-5. 1,3-Dihydro-3-(2-dimethylaminoethyl)-6-(4-pyridinyl)-2H-imidazo[4,5-b]pyridin-2-one—A mixture containing 6.67 g. of 3-amino-2-(2-dimethylaminoethylamino)-5-(4-pyridinyl)pyridine, 6.30 g. of carbonyldiimidazole and 150 ml. of dimethylformamide was stirred in a water bath at 35°-40° C. for over two hours and then at 70°-75° C. for over two hours. To the reaction mixture was added 10 ml. of water and the solvents were distilled off in vacuo. The residual brown oil was crystallized from acetonitrile (final volume of 50 ml.) and dried in a vacuum oven at 83° C. for sixteen hours to yield 6.41 g. of product. This product was recrystallized a second time from acetonitrile (final volume of 125 ml.) and dried as above to yield 5.72 g. of white solid 1,3-dihydro-3-(2-dimethylaminoethyl)-6-(4-pyridinyl)-2H-imidazo[4,5-b]pyridin-2-one, m.p. 182°–184° C.

G-6. 1,3-Dihydro-3-(3-dimethylaminopropyl)-6-(4-pyridinyl)-2H-imidazo[4,5-b]pyridin-2-one, m.p. 188°–191° C., 7.53 g., was obtained following the procedure described in Example G-5 using 14.72 g. of 3-amino-2-(3-dimethylaminopropylamino)-5-(4-pyridinyl)pyridine, 13.13 g. of carbonyldiimidazole and 300 ml. of dimethylformamide.

G-7. 1,3-Dihydro-3-[2-(4-morpholinyl)ethyl]-6-(4-pyridinyl)-2H-imidazo[4,5-b]pyridin-2-one—A mixture containing 15.11 g. of 3-amino-2-[2-(4-morpholinyl)ethylamino]-5-(4-pyridinyl)pyridine, 12.28 g. of carbonyldiimidazole and 300 ml. of dimethylformamide was stirred at 35° C. for ever one hour and then stirred at room temperature for sixteen hours. The resulting suspension was stirred with heating at 75° C. for over seventy-five minutes. To the cooled solution was added another 8.11 g. portion of carbonyldiimidazole and the resulting mixture was stirred at about 35° C. for two and one-half hours, heated at about 75° C. for forty-five minutes, and to the reaction mixture was added 15 ml. of water. The water and dimethylformamide was distilled off in vacuo and the resulting oily material was washed with n-hexane whereupon crystallization resulted. The crystalline material was then recrystallized from acetonitrile (160 ml.) and dried at 90° C. in a vacuum oven for eighteen hours to yield 11.55 g. of 1,3-dihydro-3-[2-(4-morpholinyl)ethyl]-6-(4-pyridinyl)-2H-imidazo[4,5-b]pyridin-2-one, m.p. 186°–190° C.

G-8. 1,3-Dihydro-1-methyl-6-(4-pyridinyl)-2H-imidazo[4,5-b]pyridin-2-one—A mixture containing 4 g. of 2-amino-3-methylamino-5-(4-pyridinyl)pyridine, 3.25 g. of carbonyldiimidazole and 100 ml. of dimethylformamide was stirred at room temperature for ninety minutes, with no apparent reaction taking place. The reaction mixture was then heated with stirring on a steam bath for four hours and allowed to stand overnight at room temperature. The solvent was distilled off in vacuo and the residual solid was treated with water, collected by filtration, washed with water and dried. The solid was dissolved in 6N hydrochloric acid and the excess aqueous acid distilled off in vacuo. The remaining residue was recrystallized twice from methanol using decolorizing charcoal, washed successively with ethanol and ether and dried in vacuo at 70° c. The resulting hydrochloride salt of the product was dissolved in water, the aqueous solution made the weakly basic with 10% aqueous potassium bicarbonate solution and the mixture cooled. The solid was collected, washed with water and dried in vacuo at 70° C., recrystallized from 50% ethanolicacetonitrile, and the mixture cooled overnight in ice. The solid was collected, washed with ether and dried in vacuo at 70° C. to yield 2 g. of 1,3-dihydro-1-methyl-6-(4-pyridinyl)-2H-imidazo[4,5-b]pyridin-2-one, m.p. 195°–198° C.

Following the procedure described in Example G-2 but using in place of 3-amino-2-methylamino-5-(4-pyridinyl)-pyridine a molar equivalent quantity of the appropriate 3-amino-2-$R_3$NH-5-PY-6-Q-pyridine, it is contemplated that the 1,3-dihydro-3-$R_3$-6-PY-5-Q-2H-imidazo[4,5-b]pyridin-2-ones of Example G-9 thru G-26 can be obtained.

G-9. 1,3-Dihydro-3-n-propyl-6-(3-pyridinyl)-2H-imidazo[4,5-b]pyridin-2-one.

G-10. 1,3-Dihydro-3-isopropyl-6-(2-methyl-5-pyridinyl)-2H-imidazo[4,5-b]pyridin-2-one.

G-11. 3-n-Butyl-1,3-dihydro-6-(5-methyl-3-pyridinyl)-2H-imidazo[4,5-b]pyridin-2-one.

G-12. 3-n-amyl-1,3-dihydro-6-(4-pyridinyl)-2H-imidazo[4,5-b]pyridin-2-one.

G-13. 1,3-Dihydro-3-n-hexyl-6-(3-pyridinyl)-2H-imidazo[4,5-b]pyridin-2-one.

G-14. 1,3-Dihydro-5-methyl-6-(4-pyridinyl)-2H-imidazo[4,5-b]pyridin-2-one.

G-15. 1,3-Dihydro-5-n-propyl-6-(4-pyridinyl)-2H-imidazo[4,5-b]pyridin-2-one.

G-16. 1,3-Dihydro-5-isopropyl-6-(4-pyridinyl)-2H-imidazo[4,5-b]pyridin-2-one.

G-17. 1,3-Dihydro-5-n-butyl-6-(4-pyridinyl)-2H-imidazo[4,5-b]pyridin-2-one.

G-18. 1,3-Dihydro-5-isobutyl-6-(4-pyridinyl)-2H-imidazo[4,5-b]pyridin-2-one.

G-19. 1,3-Dihydro-6-(4-pyridinyl)-5-tert.-butyl-2H-imidazo[4,5-b]pyridin-2-one.

G-20. 1,3-Dihydro-5-n-pentyl-6-(4-pyridinyl)-2H-imidazo[4,5-b]pyridin-2-one.

G-21. 1,3-Dihydro-3-(2-ethoxyethyl)-5-ethyl-6-(2-methyl-4-pyridinyl)-2H-imidazo[4,5-b]pyridin-2-one.

G-22. 5-Ethyl-1,3-dihydro-3-(2-methoxyethyl)-6-(3-pyridinyl)-2H-imidazo[4,5-b]pyridin-2-one.

G-23. 1,3-Dihydro-3-(3-methoxypropyl)-6-(4-pyridinyl)-2H-imidazo[4,5-b]pyridin-2-one.

G-24. 1,3-Dihydro-3-(2-hydroxyethyl)-5-methyl-6-(4-pyridinyl)-2H-imidazo[4,5-b]pyridin-2-one.

G-25. 1,3-Dihydro-3-(3-hydroxypropyl)-6-(4-pyridinyl)-2H-imidazo[4,5-b]pyridin-2-one.

G-26. 1,3-Dihydro-3-(2,3-dihydroxypropyl)-6-(4-pyridinyl)-2H-imidazo[4,5-b]pyridin-2-one.

Following the procedure described in Example G-8 but using in place of 2-amino-3-methylamino-5-(4-pyridinyl)-pyridine a molar equivalent quantity of the appropriate 2-amino-3-$R_1$NH-5-PY-6-Q-pyridine, it is contemplated that there can be obtained the corresponding 1,3-dihydro-1-$R_1$-6-PY-5-Q-2H-imidazo[4,5-b]pyridin-2-ones of Examples G-27 thru G-37.

G-27. 1-Ethyl-1,3-dihydro-6-(4-pyridinyl)-2H-imidazo[4,5-b]pyridin-2-one.

G-28. 1,3-Dihydro-1-n-propyl-6-(4-pyridinyl)-2H-imidazo[4,5-b]pyridin-2-one.

G-29. 1,3-Dihydro-1-isopropyl-6-(4-pyridinyl)-2H-imidazo[4,5-b]pyridin-2-one.

G-30. 1-n-Butyl-1,3-dihydro-6-(4-pyridinyl)-2H-imidazo[4,5-b]pyridin-2-one.

G-31. 1,3-Dihydro-1-(2-hydroxyethyl)-6-(4-pyridinyl)-2H-imidazo[4,5-b]pyridin-2-one.

G-32. 1,3-Dihydro-1-(2,3-dihydroxypropyl)-6-(4-pyridinyl)-2H-imidazo[4,5-b]pyridin-2-one.

G-33. 1,3-Dihydro-1-(3-methoxypropyl)-6-(4-pyridinyl)-2H-imidazo[4,5-b]pyridin-2-one.

G-34. 1,3-Dihydro-1-(2-ethoxyethyl)-6-(4-pyridinyl)-2H-imidazo[4,5-b]pyridin-2-one.

G-35. 1,3-Dihydro-1-(2-dimethylaminoethyl)-6-(4-pyridinyl)-2H-imidazo[4,5-b]pyridin-2-one.

G-36. 1,3-Dihydro-1-(3-diethylaminopropyl)-6-(4-pyridinyl)-2H-imidazo[4,5-b]pyridin-2-one.

G-37. 1,3-Dihydro-1-[2-(4-morpholinyl)ethyl]-6-(4-pyridinyl)-2H-imidazo[4,5-b]pyridin-2-one.

H. 1,3-DIHYDRO-1-R₁-3-R₃-6-PY-5-Q-2H-IMIDAZO[4,5-b]PYRIDINE-3-THIONES

H-1. 1,3-Dihydro-6-(4-pyridinyl)-2H-imidazo[4,5-b]pyridine-2-thione—To a mixture containing 18 g. of 2,3-diamino-5-(4-pyridinyl)pyridine dihydrochloride, 180 ml. of ethanol and 80 ml. of water was added 25 ml. of 2N aqueous potassium hydroxide solution and to this mixture was added 18 g. of potassium ethyl xanthate. The resulting reaction mixture was refluxed for five hours and cooled. The excess solvents were distilled off in vacuo and the residue was dissolved in water. The aqueous solution was neutralized with acetic acid and the resulting precipitate was collected and dried in vacuo at 70° C. This material was combined with another 1 g. portion obtained in another smaller run and the combined material was dissolved in 6N hydrochloric acid and the acidic solution was treated with methanol and the resulting mixture was cooled. The solid that separated was collected, washed with methanol and dried in vacuo at 70° C. This solid was recrystallized twice from 50% aqueous methanol, the second time using decolorizing charcoal, washed successively with methanol and ether and dried in vacuo at 70° C. to yield 7.5 g. of 1,3-dihydro-6-(4-pyridinyl)-2H-imidazo[4,5-b]pyridine-2-thione hydrochloride, m.p. >300° C.

H-2. 1,3-Dihydro-3-methyl-6-(4-pyridinyl)-2H-imidazo[4,5-b]pyridine-2-thione—A mixture containing 10 g. of 3-amino-2-methylamino-5-(4-pyridinyl)pyridine, 13 g. of potassium ethyl xanthate, 100 ml. of ethanol and 50 ml. of water was refluxed for twelve hours and then allowed to stand overnight at room temperature. Another 13 g. of potassium ethyl xanthate was added and refluxing was continued for an additional fourteen hours. The solvent and excess reactants were distilled off in vacuo and the residue was dissolved in water and the aqueous solution was neutralized with acetic acid. The resulting solid was collected, recrystallized twice from dimethylformamide, washed successively with ethanol and ether and dried in vacuo at 70° C. The partially hydrated product was dissolved in 1 N aqueous potassium hydroxide solution and the mixture filtered through diatomaceous earth. The filtrate was neutralized with acetic acid, the solid collected, washed with water and dried in a vacuum over at 80° C. over the weekend (three days) to yield 8.5 g. of 1,3-dihydro-3-methyl-6-(4-pyridinyl)-2H-imidazo[4,5-b]pyridine-2-thione hydrate (3:1), m.p. >300° C.

In the following run, the same compound was obtained as its hemihydrate: a mixture containing 58.2 g. of 3-amino-2-methylamino-5-(4-pyridinyl)pyridine, 93.2 g. of potassium ethyl xanthate, 580 ml. of ethanol and 200 ml. of water was refluxed with stirring overnight (about fifteen hours). An additional 90 g. of potassium ethyl xanthate was added and the reaction mixture was refluxed with stirring for another fifteen hours, and then concentrated to dryness. The residue was dissolved in water and the aqueous solution was neutralized with acetic acid. The solid was collected, washed with water, recrystallized twice from dimethylformamide, dried in a vacuum oven at 60° C. overnight to yield 50 g. of yellow powder. The yellow powder was slurried with 400 ml. of water and the aqueous mixture was made basic with 35% aqueous sodium hydroxide solution. The resulting solution was made acid with acetic acid, the precipitate was collected, washed with water and dried in a vacuum oven at 60° C. overnight to yield, as a pale yellow powder, 47 g. of 1,3-dihydro-3-methyl-6-(4-pyridinyl)-2H-imidazo[4,5-b]pyridine-2-thione hemihydrate, m.p. >300° C.

Following the procedure described in Example H-2 but using in place of 3-amino-2-methylamino-5-(4-pyridinyl)pyridine a molar equivalent quantity of the corresponding 2-R₃NH-3-R₁NH-5-PY-6-Q-pyridine, it is contemplated that there can be obtained the 1,3-dihydro-1-R₁-3-R₃-6-PY-5-Q-2H-imidazo[4,5-b]pyridine-3-thiones of Examples H-3 through H-11.

H-3. 1,3-Dihydro-1-methyl-6-(4-pyridinyl)-2H-imidazo[4,5-b]pyridine-2-thione.

H-4. 1-Ethyl-1,3-dihydro-6-(4-pyridinyl)-2H-imidazo[4,5-b]pyridine-2-thione.

H-5. 3-Ethyl-1,3-dihydro-6-(4-pyridinyl)-2H-imidazo[4,5-b]pyridine-2-thione.

H-6. 1,3-Dihydro-3-(2-hydroxyethyl)-(4-pyridinyl)-2H-imidazo[4,5-b]pyridine-2-thione.

H-7. 1,3-Dihydro-1-(2-hydroxyethyl)-6-(4-pyridinyl)-2H-imidazo[4,5-b]pyridine-2-thione.

H-8. 1,3-Dihydro-3-(2,3-dihydroxypropyl)-6-(4-pyridinyl)-2H-imidazo[4,5-b]pyridine-2-thione.

H-9. 1,3-Dihydro-3-(2-methoxyethyl)-6-(4-pyridinyl)-2H-imidazo[4,5-b]pyridine-2-thione.

H-10. 1,3-Dihydro-3,5-dimethyl-6-(4-pyridinyl)-2H-imidazo[4,5-b]pyridine-2-thione.

H-11. 1,3-Dihydro-3-(2-hydroxyethyl)-5-methyl-6-(4-pyridinyl)-2H-imidazo[4,5-b]pyridine-2-thione.

I. 1-PY-2-(DIMETHYLAMINO)ETHENYL LOWER-ALKYL KETONES

I-1. 1-(4-Pyridinyl)-2-(dimethylamino)ethenyl methyl ketone—Z mixture containing 20 g. of (4-pyridinyl)-methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for thirty minutes. TLC analysis showed a single sport, thereby indicating completion of the reaction (in another run, the reaction appeared to be complete after thirty minutes at room temperature. The reaction mixture was evaporated under reduced pressure using a rotary evaporator and a pressure of about 15 mm., thereby resulting in a crystalline residue weighing 24 g. The residue was decolorized using continuous column chromatography on alumina (about 150 g.) using refluxing chloroform. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 3-dimethylamino-4-(4-pyridinyl)-3-buten-2-one.

The above preparation can be carried out using in place of hexamethylphosphoramide other solvents, e.g., dimethylformamide, acetonitrile or others noted above; however, hexamethylphosphoramide was conveniently used since (4-pyridinyl)methyl methyl ketone was conveniently prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over twenty minutes 210 cc. of 2.4 M n-butyllithium in n-hexane and the reaction mixture was stirred for about thrity-five minutes at about 0°–5° C. To the cold solution was added dropwise over a period of ten minutes 90 cc. of dry hexamethylphosphoramide (no temperature change) and a resulting light yellow solution was stirred for fifteen minutes. To the cold solution at 0° C. was added a solution of 50 cc. of 4-picoline in 150 cc. of dry tetrahydrofuran over a fifteen minute period and stirring was continued for thirty minutes at 0° C. Next, a mixture containing 50 cc. of dry ethyl acetate and 150 cc. of tetrahydrofuran was added over a fifteen minutes period (temperature rose from 0° to about 6° C.) and the resulting mixture was stirred for twenty minutes at 0° C. The ice bath was then removed and stirring continued for another ninety minutes whereupon the temperature of the reaction mixture rose to about 25° C. The reaction mixture was then cooled in an ice bath and to it was added 60 cc. of acetic acid over a period of about thirty minutes. The tetrahydrofuran was distilled off using a rotary evaporator in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of a mixture consisting primarily of the desired product and hexamethylphosphoramide. Another run using the same quantities was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g. b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to consist of a 2:3 mixture by weight of (4-pyridinyl)-methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively and the monoacetate or monohydrochloride salt in aqueous solution.

I-2. 1-(4-Pyridinyl)-2-(dimethylamino)ethenyl ethyl ketone—A mixture containing 87.5 g. of (4-pyridinyl)-methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for forty-five minutes. The methanol formed by the reaction was distilled off in vacuo using a rotary evaporator and the remaining material was distilled under reduced pressure to yield two fractions, one boiling at 45°–80° C. at 0.5 mm. and the second at 90°–95° C. at 0.5 mm. After TLC analysis showed predominantly only a single spot for each fraction, the two fractions were combined (135 g.) and taken up in 600 cc. of chloroform. The resulting solution was washed with two 300 cc. portions of water and the water was back extracted with three 100 cc. portions of chloroform. The combined chloroform solution was dried over anhydrous sodium sulfate and decolorized by running it through 300 cc. of alumina in a 500 cc. continuous extraction column followed by extraction with efluxing chloroform. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained by passing the mother liquor through the continuous extraction column and using refluxing chloroform as the solvent.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°–5° C. was added 210 cc. of 2.4 n-butyllithium in n-hexane and the resulting mixture was stirred for thirty minutes. Next was added over a ten minute period 90 cc. of hexamethylphosphoramide followed by stirring of the mixture for fifteen minutes. Then was added over a fifteen minute period a solution of 48 cc. of 4-picoline in 150 cc. of tetrahydrofuran followed by stirring for thirty minutes at about 0° C. The ice/acetone bath cooling the reaction mixture was replaced with a dry ice/acetone bath and to the reaction mixture was added over a twenty minute period a mixture of 75 cc. of ethyl propionate in an equal volume of tetrahydrofuran. The reaction mixture was then allowed to warm up to room temperature over a period of about ninety minutes and then was warmed at about 35° C. for thirty minutes. The mixture was next cooled in an ice/acetone bath and to it was added 60 cc. of glacial acetic acid over thirty minutes. The resulting pale yellow suspension was diluted with 200 cc. of water. The mixture was extracted with three 150 cc. portions of ethyl acetae and the ethyl acetate extract was back washed with saline solution. The extract was heated in vacuo to remove the ethyl acetate and the residue ws taken up again with ethyl acetate. The solution was washed with water and then heated in vacuo to remove the ethyl acetate followed by heating the residue in vacuo at 50° C. for about thirty minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)-methyl ethyl ketone and hexamethylphosphoramide in a respective molar ratio of 1:1.55, that is, 35% or 0.35×256=90 g. of said ketone.

Following the procedure described in Example I-2 but using a molar equivalent quantity of the appropriate PY-methyl lower-alkyl ketone (II) in place of (4-pyridinyl)methyl ethyl ketone, it is contemplated that the corresponding 1-PY-2-(dimethylamino(ethenyl lower-alkyl ketones of Examples I-3 thru I-17 can be obtained.

I-3. 1-(3-Pyridinyl)-2-(dimethylamino)ethenyl methyl ketone using (3-pyridinyl)methyl methyl ketone.

I-4. 1-(4-Pyridinyl)-2-(dimethylamino)ethenyl n-propyl ketone using (4-pyridinyl)methyl n-propyl ketone.

I-5. 1-(4-Pyridinyl)-2-(dimethylamino)ethenyl isopropyl ketone using (4-pyridinyl)methyl n-butyl ketone.

I-6. 1-(4-Pyridinyl)-2-(dimethylamino)ethenyl n-butyl ketone using (4-pyridinyl)methyl n-butyl ketone.

I-7. 1-(4-Pyridinyl)-2-(dimethylamino)ethenyl isobutyl ketone using (4-pyridinyl)methyl isobutyl ketone.

I-8. 1-(4-Pyridinyl(-2-(dimethylamino)ethenyl tert.-butyl ketone using (4-pyridinyl)methyl tert.-butyl ketone.

I-9. 1-(4-Pyridinyl)-2-(dimethylamino)ethenyl n-pentyl ketone using (4-pyridinyl)methyl n-pentyl ketone.

I-10. 1-(2-Methyl-4-pyridinyl)-2-(dimethylamino)ethenyl ethyl ketone using (2-methyl-4-pyridinyl)methyl ethyl ketone. I-11. 1-(3-Pyridinyl)-2-(dimethylamino)ethenyl ethyl ketone using (3-pyridinyl)methyl ethyl ketone.

J. 1,2-DIHYDRO-6-(LOWER-ALKYL)-2-OXO-5-PY-NICOTINONITRILES

J-1. 1,2-Dihydro-6-methyl-2-oxo-5-(4-pyridinyl)-nicotinonitrile, alternatively named 1,6-dihydro-2-methyl-6-oxo[3,4'-bipyridin]-5-carbonitrile—To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary evaporator to a volume of about 80 cc. The concentrate was treated with about 160 cc. of acetonitrile and the resulting mixture was stirred on a rotary evaporator with warming until homogeneous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)-nicotinonitrile, m.p. 300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a small pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)-nicotinonitrile and the appropriate acid, e.g., lactic acid or hydrochloric acid, to prepare respectively the monolactate or monohydrochloride salt in aqueous solution.

J-2. 6-Ethyl-1,2-dihydro-2-oxo-5-(4-pyridinyl)-nicotinonitrile, alternatively named 2-ethyl-1,6-dihydro-6-oxo-[3,4'-bipyridin]-5-carbonitrile, m.p. >300° C., 11.6 g., was prepared following the procedure described above in Example J-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

Following the procedure described in Example D-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone, it is contemplated that the corresponding 1,2-dihydro-2-oxo-5-PY-6-R-nicotinonitriles of Examples J-3 thru J-17 can be obtained.

J-3. 1,2-Dihydro-6-methyl-2-oxo-5-(3-pyridinyl)-nicotinonitrile, using 1-(3-pyridinyl)-2-(dimethylamino)ethenyl methyl ketone.

J-4. 1,2-Dihydro-2-oxo-6-n-propyl-5-(4-pyridinyl)-nicotinonitrile, using 1-(4-pyridinyl)-2-(dimethylamino)ethenyl n-propyl ketone.

J-5. 1,2-Dihydro-6-isopropyl-2-oxo-5-(4-pyridinyl)-nicotinonitrile, using 1-(4-pyridinyl)-2-(dimethylamino)ethenyl isopropyl ketone.

J-6. 6-n-Butyl-1,2-dihydro-2-oxo-5-(4-pyridinyl)-nicotinonitrile, using 1-(4-pyridinyl)-2-(dimethylamino)ethenyl n-butyl ketone.

J-7. 1,2-Dihydro-6-isobutyl-2-oxo-5-(4-pyridinyl)-nicotinonitrile, using 1-(4-pyridinyl)-2-dimethylamino)ethenyl isobutyl ketone.

J-8. 1,2-Dihydro-2-oxo-5-(4-pyridinyl-6-tert.-butyl-nicotinonitrile, using 1-(4-pyridinyl)-2-(dimethylamino)ethenyl tert.-butyl ketone.

J-9. 1,2-Dihydro-2-oxo-6-n-pentyl-5-(4-pyridinyl)-nicotinonitrile, using 1-(4-pyridinyl)-2-(dimethylamino)ethenyl n-pentyl ketone.

J-10. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone.

J-11. 6-Ethyl-1,2-dihydro-2-oxo-5-(3-pyridinyl)-nicotinonitrile, using 1-(3-pyridnyl)-2-(dimethylamino)ethenyl ethyl ketone.

K. 1,2-DIHYDRO-6-(LOWER-ALKYL)-2-OXO-5-PY-NICOTINIC ACIDS

Following the procedure described in Example B-1 of U.S. Pat. No. 4,072,746 but using in place of 1,2-dihydro-2-oxo-5-(4-pyridinyl)nicotinonitrile a molar equivalent quantity of the corresponding 1,2-dihydro-2-oxo-5-PY-6-(lower-alkyl)nicotinonitrile, it is contemplated that there can be obtained the 1,2-dihydro-2-oxo-5-PY-6-(lower-alkyl)nicotinic acids of Examples K-1 through K-11.

K-1. 1,2-Dihydro-6-methyl-2-oxo-5-(4-pyridinyl)-nicotinic acid.

K-2. 6-Ethyl-1,2-dihydro-2-oxo-5-(4-pyridinyl)nicotinic acid.

K-3. 1,2-Dihydro-6-methyl-2-oxo-5-(3-pyridinyl)-nicotinic acid.

K-4. 1,2-Dihydro-2-oxo-6-n-propyl-5-(4-pyridinyl)-nicotinic acid.

K-5. 1,2-Dihydro-2-oxo-6-isopropyl-5-(4-pyridinyl)-nicotinic acid.

K-6. 6-n-Butyl-1,2-dihydro-2-oxo-5-(4-pyridinyl)-nicotinic acid.

K-7. 1,2-Dihydro-6-isobutyl-2-oxo-5-(4-pyridinyl)-nicotinic acid.

K-8. 1,2-Dihydro-2-oxo-5-(4-pyridinyl)-6-tert.-butyl-nicotinic acid.

K-9. 1,2-Dihydro-2-oxo-6-n-pentyl-5-(4-pyridinyl)-nicotinic acid.

K-10. 6-Ethyl-1,2-dihydro-5-(2-methyl-4-pyridinyl)-2-oxonicotinic acid.

K-11. 6-Ethyl-1,2-dihydro-2-oxo-5-(3-pyridinyl)nicotinic acid.

L. 6-(LOWER-ALKYL)-3-NITRO-5-PY-2(1H)-PYRIDINONES

Following the procedure described in Example C-1 of U.S. Pat. No. 4,072,746 but using in place of 1,2-dihydro-2-oxo-5-(4-pyridinyl)nicotinic acid a molar equivalent quantity of the corresponding 1,2-dihydro-2-oxo-5-PY-6-(lower-alkyl)-nicotinic acid, it is contemplated that there can be obtained the 3-nitro-5-PY-6-(lower-alkyl)-2(1H)pyridinones of Examples L-1 through L-11.

L-1. 6-Methyl-3-nitro-5-(4-pyridinyl)-2(1H)-pyridinone.

L-2. 6-Ethyl-3-nitro-5-(4-pyridinyl)-2(1H)-pyridinone.

L-3. 6-Methyl-3-nitro-5-(3-pyridinyl)-2(1H)-pyridinone.

L-4. 3-Nitro-6-n-propyl-5-(4-pyridinyl)-2(1H)-pyridinone.

L-5. 3-Nitro-6-isopropyl-5-(4-pyridinyl)-2(1H)-pyridinone.

L-6. 6-n-Butyl-3-nitro-5-(4-pyridinyl)-2(1H)-pyridinone.

L-7. 6-Isobutyl-3-nitro-5-(4-pyridinyl)-2(1H)-pyridinone.

L-8. 3-Nitro-5-(4-pyridinyl)-6-tert.-butyl-2(1H)-pyridinone.

L-9. 3-Nitro-6-n-pentyl-5-(4-pyridinyl)-2(1H)-pyridinone.

L-10. 6-Ethyl-5-nitro-5-(2-methyl-4-pyridinyl)-2(1H)-pyridinone.

L-11. 6-Ethyl-3-nitro-5-(3-pyridinyl)-2(1H)-pyridinone.

M. 6-(LOWER-ALKYL)-5-PY-2(1H)-PYRIDINONES

Following the alternative procedure described in Example C-1 from line 59 of column 15 to line 2 of column 16 of U.S. Pat. No. 4,072,746 but using in place of 1,2-dihydro-2-oxo-5-(4-pyridinyl)nicotinonitrile a molar equivalent quantity of the corresponding 1,2-dihydro-2-oxo-5-PY-6-(lower-alkyl)-nicotinonitrile, it is contemplated that there can be obtained the 5-PY-6-(lower-alkyl)-2(1H)-pyridinones of Examples M-1 through M-11.

M-1. 6-Methyl-5-(4-pyridinyl)-2(1H)-pyridinone.
M-2. 6-Ethyl-5-(4-pyridinyl)-2(1H)-pyridinone.
M-3. 6-Methyl-5-(3-pyridinyl)-2(1H)-pyridinone.
M-4. 6-n-Propyl-5-(4-pyridinyl)-2(1H)-pyridinone.
M-5. 6-Isopropyl-5-(4-pyridinyl)-2(1H)-pyridinone.
M-6. 6-n-Butyl-5-(4-pyridinyl)-2(1H)-pyridinone.
M-7. 6-Isobutyl-5-(4-pyridinyl)-2(1H)-pyridinone.
M-8. 5-(4-Pyridinyl)-6-tert.-butyl-2(1H)-pyridinone.
M-9. 6-n-Pentyl-5-(4-pyridinyl)-2(1H)-pyridinone.
M-10. 6-Ethyl-5-(2-methyl-4-pyridinyl)-2(1H)-pyridinone.
M-11. 6-Ethyl-5-(3-pyridinyl)-2(1H)-pyridinone.

The usefulness of the compounds of formula I or salts thereof as cardiotonic agents is demonstrated by their effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formula I or pharmaceutically-acceptable acid-addition salts thereof at doses of 1, 3, 10, 30, 100 and/or 300 µg./ml., were found to cause significant increases, that is, greater than 25% in papillary muscle force and significant increases, that is, greater than 25%, in right atrial force, while causing a lower percentage increase (about one-third or less than the percentage increase in right atrial force or papillary muscle force) in right atrial rate. For example, when tested at said dose levels by this procedure, the following preferred compounds were found to cause increases of 70% and greater in papillary muscle force and/or right atrial force: the compounds of Examples G-1, G-2, G-3, G-4, G-5, G-7, G-8, H-1 and H-2.

When tested by said anesthetized dog procedure, the compounds of formula I or pharmaceutically-acceptable acid-addition salts thereof at doses of 0.1, 0.3, 1.0, 3.0 and/or 10 mg./kg. administered intravenously were found to cause significant increases, that is, 25% or greater, in cardiac contractile force or cardiac contractility with lower changes in heart rate and blood pressure. For example, when tested at said dose levels by this procedure, the following preferred compounds were found to cause increases of 70% and greater in contractile force and lower changes in heart rate and blood pressure: the compounds of Examples G-1, G-2, G-3, G-4, G-5, H-1 and H-2. When tested orally in the unanesthetized dog at 1.0, 3.0 and 10.0 mg./kg., the compound of Example G-4 was found to cause cardiac contractile force increases of 30, 54 and 104%, respectively, while causing respective heart rate increases of 9, 19 and 31%, and respective diastolic blood pressure changes of +4%, −6% and −1%.

When screened by other standard pharmacological test procedures, some embodiments of the compounds of formula I or salts were found to have antihypertensive and/or bronchodilator activities. For example, the compounds of Examples G-1 and G-2 were found to have oral $AHD_{40}$ values of 40 and 30 mg./kg. when tested in the spontaneously hypertensive rat; similarly, the compounds of Examples G-4 and G-5 were found to have low antihypertensive activities ($AHD_{40}$ values of 50 mg./kg. p.o.) when tested by this procedure. When tested orally at 100 mg./kg., the compounds of Examples G-1, G-2 and G-3 were each found to have bronchodilator activity by inhibiting bronchoconstriction induced by histamine, acetylcholine or immune complex in guinea pigs.

The present invention includes within its scope a cardiotonic composition for increasing cardiac contractility, said composition comprising a pharmaceutically-acceptable carrier and, as the active component thereof, the cardiotonic compound of formula I or pharmaceutically-acceptable acid-addition salt thereof. The invention also includes within its scope the method for increasing cardiac contractility in a patient requiring such treatment which comprises administering to such patient an effective amount of cardiotonic compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. The process which comprises reacting 2-$R_3$NH-3-$R_1$NH-5-PY-6-Q-pyridine with urea or carbonyldiimidazole to produce 1,3-dihydro-1-$R_1$-3-$R_3$-6-PY-5-Q-2H-imidazo[4,5-b]pyridin-2-one or with an alkali metal xanthate, thiourea or thiocarbonyldiimidazole to produce 1,3-dihydro-1-$R_1$-3-$R_3$-6-PY-5-Q-2H-imidazo[4,5-b]pyridine-2-thione, where Q is hydrogen or lower-alkyl, $R_1$ and $R_3$ each are hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, at least one of $R_1$ or $R_3$ being hydrogen, and PY is 4- or 3-pyridinyl or 4- or 3-pyridinyl having one or two lower-alkyl substituents.

* * * * *

UNITED STATES PATENT AND TRADEMARK OFFICE
CERTIFICATE OF CORRECTION

PATENT NO. : 4,309,537
DATED : January 5, 1982
INVENTOR(S) : George Y. Lesher et al.

It is certified that error appears in the above—identified patent and that said Letters Patent are hereby corrected as shown below:

Column 2, formula IB, should read

-- 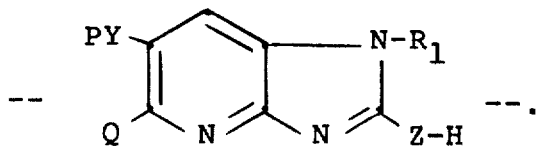 --.

Column 3, line 64, "means" should be deleted.

Signed and Sealed this

Twenty-third Day of November 1982

[SEAL]

Attest:

Attesting Officer

GERALD J. MOSSINGHOFF

Commissioner of Patents and Trademarks